United States Patent [19]

Tanaka et al.

[11] Patent Number: 5,183,883
[45] Date of Patent: Feb. 2, 1993

[54] CONJUGATE OF ADRIAMYCIN AND CYCLODEXTRIN

[75] Inventors: Hiroshi Tanaka, Chigasaki; Kaichiro Kominato, Yamato; Takeo Yoshioka, Ayase; Hiroshi Iguchi, Yokohama; Shin-ichi Hirano, Chigasaki; Yasuo Okajima, Fujisawa; Reijko Yamamoto, Sagamihara; Masataka Shirai, Tokyo; Hiroshi Nishida, Yokosuka; Hiroshi Tone, Yokohama; Rokuro Okamoto, Fujisawa, all of Japan

[73] Assignee: Mercian Corporation, Tokyo, Japan

[21] Appl. No.: 766,791

[22] Filed: Sep. 27, 1991

[30] Foreign Application Priority Data

Sep. 28, 1990 [JP] Japan ................................ 2-257209

[51] Int. Cl.$^5$ ............................................. C07K 15/24
[52] U.S. Cl. ...................................... 563/6.4; 536/112
[58] Field of Search .................... 536/6.9, 112; 519/34

[56] References Cited

U.S. PATENT DOCUMENTS 4,870,058  9/1989  Horton et al. ...................... 536/6.4

FOREIGN PATENT DOCUMENTS 0116222  8/1984  European Pat. Off. .
3191802  8/1988  Japan ................................. 536/122

OTHER PUBLICATIONS

Chemical Abstracts, 112, 21, p. 75, 191933v (May 21, 1990).

Chemical Abstracts, 111, p. 32, 89934p (Sep. 11, 1989).

Primary Examiner—John W. Rollins
Assistant Examiner—Elli Peselev
Attorney, Agent, or Firm—Wenderoth, Lind & Ponack

[57] ABSTRACT

Adriamycin derivatives represented by formula (I)

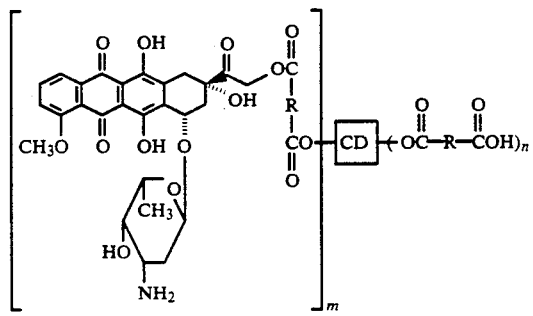

wherein
R denotes a divalent hydrocarbon group,
CD denotes a cyclodextrin residue,
m is 1 to 8, and
n is 0 to 8.

The compounds exhibit excellent anti-cancer activity over a wide administration range, have low toxicity and sustained release, and maintain activity for a long period of time; thus, they are quite useful as an anti-cancer agent.

8 Claims, No Drawings

CONJUGATE OF ADRIAMYCIN AND CYCLODEXTRIN

This invention relates to novel adriamycin derivatives, and more specifically to a conjugate of adriamycin and cyclodextrin having less side effects and good durability of a blood level and exhibiting excellent therapeutic effects.

Daumomycin (see U.S. Pat. No. 3,616,242) and adriamycin (see U.S. Pat. No. 3,590,028) have been known as anticancer anthracycline compounds. Especially adriamycin is an excellent anti-cancer agent which has been clinically widely used. However, adriamycin exhibits strong side effects such as cardiotoxicity and bone-marrow suppression (see, e.g., S. K. Carter: Cancer Chemotherapy and Pharmacology, vol. 4, pp. 5-10, 1980), and alleviation of these side effects is therefore one big problem.

Extensive studies to eliminate this problem have been widely made so far, and in recent years, studies have been increasingly made especially on a drug delivery system requiring alleviation of toxicity, maintenance of a blood level and affinity for cancer cells. For example, Japanese Laid-open Patent Application No. 67,490/1985 aims to alleviate toxicity of anthracycline antibiotics and improve anti-cancer activity thereof by conjugating said antibiotics with a divinyl ethermaleic anhydride copolymer. Japanese Laid-open Patent Application No. 254,598/1986 discloses peptide derivatives of anthracyclin compounds having excellent affinity for cancer cells. Moreover, in F. Levi-Schaffer, Cancer Treatment Reports, vol. 66, pp. 107-114, 1982, it is reported that toxicity of daunomycin is decreased by conjugating daunomycin with dextran.

The present inventors have made assiduous investigations to develop safe adriamycin having low toxicity, having a wide-ranging dosage and excelling in therapeutic effect, and have consequently found that the purpose can be achieved by chemically conjugating adriamycin with cyclodextrin via a dicarboxylate. This finding has led to completion of this invention.

Thus, according to this invention, there are provided adriamycin derivatives represented by formula (I),

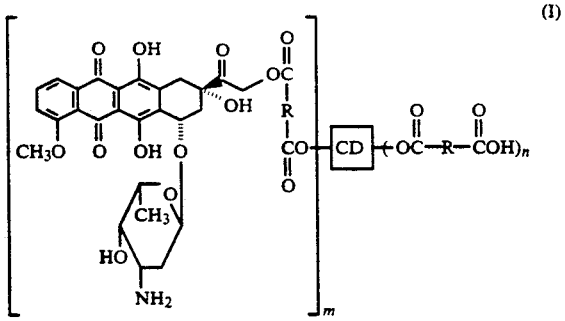

wherein
R denotes a divalent hydrocarbon group,
CD denotes a cyclodextrin residue,
m is 1 to 8, and
n is 0 to 8.

In the above formula (I), the divalent hydrocarbon group denoted by R is a residue obtained by removing two carboxyl groups from a dicarboxylic acid molecule. Examples thereof include alkylene groups such as methylene, ethylene, 1,2- or 1,3-propylene, and 1,2-, 1,3- or 1,4-butylene, especially alkylene groups having 1 to 6 carbon atoms, more preferably alkylene groups having 1 to 4 carbon atoms; alkenylene groups such as —CH=CH—; cycloalkylene groups such as 1,2-cyclohexylene, especially cycloalkylene groups having 5 to 7 carbon atoms; and arylene groups such as 1,2-phenylene, and 2,3- or 1,8-naphthalene.

The cyclodextrin residue denoted by CD may be derived from $\alpha$-, $\beta$- and $\gamma$-cyclodextrins. Above all, the cyclodextrin residue derived from $\gamma$-cyclodextrin is preferable.

Further, m which is the number of the adriamycin moiety bound to the cyclodextrin residue via the dicarboxylate represented by the formula $$(-OOC-R-COO-)$$

is 1 to 8, preferably 1 to 2. When m is larger than n, a (m-n) number of amino groups may be present in the form of a hydrochloride, a sulfate, an acetate or a tartrate.

When n is larger than m, a (n-m) number of carboxyl groups may be present in the form of a sodium, calcium, or ammonium salt.

Meanwhile, n is 0 to 8, preferably 0 to 2.

The adriamycin derivatives of formula (I) provided by this invention can be prepared by, for example, acylating cyclodextrin, preferably $\gamma$-cyclodextrin with a dicarboxylic acid represented by formula (II)

$$HOOC-R-COOH \qquad (II)$$

wherein R is as defined above,
or its acyl-forming derivatives, and reacting the resulting acylated cyclodextrin represented by formula (III)

$$CD(-OOC-R-COOY)_{m+n} \qquad (III)$$

wherein
R, CD, m and n are as defined above, and
Y denotes a cation.

In the acylation reaction at the first stage, the hydroxyl group at the 2-position, 3-position and/or 6-position of the glucose unit constituting cyclodextrin is acylated.

Examples of the dicarboxylic acid of formula (II) which is used in the acylation reaction are succinic acid, glutaric acid, adipic acid, maleic acid, phthalic acid, naphthalenedicarboxylic acid, and cyclohexanedicarboxylic acid. Examples of the acyl-forming derivatives are anhydrides and acid halides. Of these, the anhydrides are preferable.

Thus, when cyclodextrin is reacted with the dicarboxylic acid anhydride of formula (II), it is advisable that cyclodextrin is dissolved in an organic solvent such as N,N-dimethylformamide or dimethylsulfoxide, 0.2 to 16 mols, preferably 0.2 to 4 mols. more preferably 0.2 to 2 mols, per mol of cyclodextrin, of the dicarboxylic acid anhydride is dissolved in the solution, and 0.2 to 32 mols, preferably 0.2 to 4 mols, per mol of cyclodextrin, of a basic catalyst, e.g., a trialkylamine such as triethylamine or N,N-diisopropylethylamine is added to this solution, and the reaction is run at a temperature of about 0° to 50° C., usually room temperature. The acylated cyclodextrin wherein Y in formula (III) is a cation corresponding to the base used.

The thus acylated cyclodextrin can successively be reacted, as the acylation reaction, at the second stage, directly with 1/16 to 1 mol, per mol of the starting dicarboxylic acid anhydride, of a 14-halodaunomycin salt, preferably 14-bromodaumnomycin hydrochloride (described in U.S. Pat. No. 3,803,124) at a temperature of usually about 0° to 50° C., preferably about 10° to 30° C. The thus obtained adriamycin derivatives of formula (I) in this invention can be obtained as a precipitate by a method known per se, for example, by adding a suitable organic solvent (e.g., chloroform, isopropyl ether, and ethanol) to the reaction mixture. In case purification is needed, separation and purification can be performed by a usual method such as reversed phase column chromatography using an octadecyl silica gel (ODS).

During the study, the present inventors have discovered that derivatives in which adriamycin has been selectively introduced into only the hydroxyl group in the 6-position of the glucose unit constituting cyclodextrin can be prepared by the following method.

Cyclodextrin is dissolved in a suitable organic solvent such as N,N-dimethylformamide or dimethyl sulfoxide, an excessive amount of an aromatic tertiary amine such as pyridine, collidine or N,N-dimethylaniline, preferably pyridine, is added as a basic catalyst, and 0.2 to 8 mols, preferably 0.2 to 4 mols, more preferably 0.2 to 2 mols, per mol of cyclodextrin, of the dicarboxylic acid anhydride is added with stirring, followed by conducting a reaction at a temperature of about 0° to 100° C., preferably about 10° to 50° C. for a few hours. A suitable organic solvent such as chloroform, isopropyl ether, acetone or ethyl acetate is added to the reaction mixture after the reaction to precipitate the product so that 6-O-(acyl)$_k$-cyclodextrin (wherein k is m+n and 1 to 8) can be obtained as a main product. This product can be used as such in the next reaction or can be purified by an ordinary means. Table 1 shows the reaction conditions and the reaction results when only the hydroxyl group in the 6-position of γ-cyclodextrin is selectively acylated.

TABLE 1

| | Reaction conditions | | Acylated* products |
|---|---|---|---|
| acid anhydride | molar ratio of acid anhydride/γCD | volume ratio of base/ solvent | formation ratio of 6-O-acyl/2 or 3-O-acyl |
| PA | 1/3 | Pyr | 13.6/1 |
| SA | 1/1 | Pyr/DMF = 5/1 | 4.6/1 |
| NA | 1/2 | Pyr/DMF = 5/1 | 14.0/1 |
| CA | 1/2 | Pyr/DMF = 5/1 | 14.7/1 |

(Note)
PA: phthalic anhydride
SA: succinic anhydride
NA: 2,3-naphthalenedicarboxylic anhydride
CA: 1,2-cis-cyclohexanedicarboxylic anhydride
Pyr: pyridine
DMF: N,N-dimethylformamide
*acylated product formation ratio is a peak ratio by HPLC analysis. The conditions of the HPLC analysis are as follows.
Column: YMC-PACK A312 S-5 120A ODS
Mobile phase: 0.1% acetic acid/methanol = 3:1 to 9:1
Detection: RI or UV (254 nm)
Flow rate: 1.0 ml/min In the acylation reaction at the second stage, 1 mol of 6-O-(acyl)$_k$-cyclodextrin is dissolved in a suitable organic solvent such as N,N-dimethylformamide or dimethylsulfoxide, preferably (½ to 2 k) mol of an organic base, preferably a trialkylamine such as triethylamine or N,N-diisopropylethylamine is added, and (¼ k to k) mol of a 14-halodaunomycin salt, preferably 14-bromodaunomycin hydrochloride is added under stirring, followed by conducting the reaction at a temperature of about 0° to 50° C., preferably about 10° to 30° C. for a few hours. After the reaction, a suitable organic solvent such as chloroform, isopropyl ether or ethyl acetate is added to the reaction mixture to precipitate the product, so that a crude adriamycin (14-position)-dicarboxylate-(6-position) cyclodextrin conjugate can be obtained. This product can be further purified by a usual means if required. It can be isolated and purified by reversed phase silica gel column chromatography using octadecyl silica gel (ODS).

The adriamycin derivatives provided by this invention show sustained release for a long period of time, and exhibit outstanding anti-cancer activity over a wide dosage range as is clear from an anti-cancer activity test using mice which will be later described. Moreover, the adriamycin derivatives of this invention are quite alleviated in toxicity compared to adriamycin, and their usefulness as an anti-cancer agent is much expected.

Sustained release test

One milligram of each of the adriamycin derivatives obtained in Examples 1, 2, 3, 4, 5 and 6 to be described later was dissolved in 0.0067 M phosphoric acid buffer physiological saline solution made by Bioproducts, Inc. (initial pH = 7.36 − 7.37), and the solution was kept at 37° C. The amount of adriamycin liberated in the solution was analyzed by HPLC [column = YMC Pack A-312 S-5 120A ODS; mobile phase = 0.05M ammonium formate buffer (pH = 4.0):- acetonitrile = 7:4, flow rate = 1 ml/min; measuring wavelength = 254 nm; retention time of adriamycin under the present conditions = 3.8 minutes].

Consequently, a 50 % released time of adriamycin from the adriamycin derivatives is as follows, and sustained release was confirmed.

ASC in Example 1 = about 1 hour
APC in Example 2 = about 20 hours
6-ASC in Example 3 = about 3 hours
6-APC in Example 4 = about 45 hours
6-ANC in Example 5 = about 65 hours
6-ACC in Example 6 = >70 hours

Cytotoxicity test $5 \times 10^4$ cells/ml of mouse leukemia cells were inoculated in a RPMI1640 culture medium containing 10% horse serum, and the compound of the present invention was added to this such that the final concentration became 0.001 to 10.0 μg/ml. Cultivation was conducted in a carbon dioxide gas incubator (air containing 5% carbon dioxide gas) at 37° C. for 48 hours. After dyeing with trypan blue, living cells were counted, and the $IC_{50}$ values (50% inhibitory concentrations) were obtained by comparing with living cells of untreated controls. The results are shown in Table 2.

TABLE 2

| Compound | Cytotoxicity, $IC_{50}$ (μg/ml) | Compound | Cytotoxicity, $IC_{50}$ (μg/ml) |
|---|---|---|---|
| Adriamycin | 0.058 | Example 3, 6-ASC | 0.21 |
| Example 1, ASC | 0.18 | Example 4, 6-APC | 0.49 |
| Example 2, APC | 0.32 | Example 5, 6-ANC | 0.79 |
| | | Example 6, 6-ACC | 2.07 |

The results of this test well correspond to the sustained release rate of adriamycin shown in the aforesaid sustained release test. This also confirmed that the compound of this invention has sustained release. [Test of anti-cancer activity to L1210 leukemia mice]

$1 \times 10^5$ L1210 leukemia cells were inoculated into $CDF_1$ mice intraperitoneally, and 24 hours later, the aqueous solution of the compound of this invention was intraperitoneally administered successively over 10 days. Test groups, each consisting of 6 mice, were fed and observed for 60 days, and percent prolongation of life (T/C; %) was found. The results are shown in Table 3.

TABLE 3

| Compound | Dose mg/kg/day | | Anti-cancer activity | |
|---|---|---|---|---|
| | | | T/C (%) | Survived mice/ test mice |
| Adriamycin hydrochloride | 5.00 | | 132 | 0/6 |
| | 2.50 | | 177 | 0/6 |
| | 1.25 | | 255 | 0/6 |
| | 0.63 | | 218 | 0/6 |
| | 0.31 | | 170 | 0/6 |
| ASC (Compound of Example 1) | 38.17 | (10.0) | 159 | 0/6 |
| | 26.72 | (7.0) | 193 | 0/6 |
| | 19.08 | (5.0) | 552 | 3/6 |
| | 13.36 | (3.5) | 545 | 3/6 |
| | 9.54 | (2.5) | 207 | 0/6 |
| APC (Compound of Example 2) | 156.25 | (40.0) | 143 | 0/6 |
| | 78.13 | (20.0) | 475 | 0/6 |
| | 39.06 | (10.0) | 468 | 2/6 |
| | 19.53 | (5.0) | 234 | 0/6 |
| | 9.77 | (2.5) | 164 | 0/6 |

( ): Amount calculated as adriamycin

Toxicity test $LD_{50}$ $LD_{50}$ given when the adriamycin derivatives of this invention were intravenously administered once in mice is as follows.

Adriamycin derivative (ASC) in Example 1:
200–400 mg/kg (50–100 mg/kg as adriamycin)
Adriamycin derivative (APC) in Example 2:
555 mg/kg (147 mg/kg as adriamycin)
Adriamycin: 9.8 mg/kg (intravenous injection in mice;
see "Collection of Medicaments in Japan" compiled by Nippon Iyaku Joho Center, Yakugyo Jihosha, 1989)

As stated above, the adriamycin derivatives of this invention exhibit excellent anti-cancer activity against L1210 leukemia over a wide administration range, have low toxicity and sustained release, and maintain activity for a long period of time; thus, they are quite useful as an anti-cancer agent.

When the adriamycin derivatives of this invention are used in therapy and treatment of cancers as an anti-cancer agent, said derivatives can be administered at a dose of usually 0.1 to 20 mg/kg/day calculated as adriamycin orally, parenterally, preferably intravenously or intra-arterially.

The adriamycin derivatives of this invention can be formulated into a dosage form according to the administration route. For example, said derivatives can be formulated into an injection together with pharmaceutically acceptable additives such as mannitol, lactose, etc. by a method known per se.

This invention will be illustrated more specifically by the following Examples.

EXAMPLE 1

Preparation of an adriamycin-succinic acid-γ-cyclodextrin conjugate (ASC)

γ-CD (520 mg, 0.4 mmol) and 80 mg (0.8 mmol) of succinic anhydride were dissolved in 10 ml of DMF, and 140 μl (1.0 mmol) of triethylamine was then added, followed by conducting the reaction at room temperature for hours. Successively, 257 mg (0.4 mmol) of 14-bromodaunomycin hydrochloride was added to this solution, and the reaction was run at room temperature for 15 hours. Under ice cooling, 20 ml of chloroform was added to the reaction mixture, and the resulting precipitate was filtered, washed with 30 ml of methanol, and then dried to obtain 730 mg of a red powder. Further, 200 mg of this powder was purified by ODS column (ODS-A 120-350/250 of YMC CO., LTD.; eluent - water/acetonitrile/acetic acid=700:300:1; column diameter 1.6 cm, height 20 cm). Fractions having purity of 99% or higher were collected under conditions of HPLC-1 to be described later. There resulted 115 mg of the above-captioned compound (ASC). ASC is composed of three main components (products 1–3).

Physicochemical properties of this compound are shown below.

UV visible (in water; λmax):
484, 290, 254, 234 nm.
Adriamycin content of the product by 484 nm absorbance: 26.8%.
IR (KBr): 3380, 2900, 1725, 1610, 1580, 1405, 1280, 1150, 1025 cm$^{-1}$.
HPLC-1: ASC-(products 1–3) retention. time=2.1. minutes. Column: YMC-Pack A 312 S-5 120A ODS Mobile phase: 0.05M ammonium formate buffer. (pH=4.0): acetonitrile=6:4. Flow rate: 1 ml/min. Detection: UV 254 nm.
HPLC-2: ASC-product 1 retention time=9.7 minutes. ASC-product 2 retention time=10.7 minutes. ASC-product 3 retention time=11.8 minutes. Column: YMC-Pack A-312 S-5 120A ODS Mobile phase: 0.05M ammonium formate buffer.
(pH=4.0):methanol:acetonitrile=6:3:1. Flow rate: 1.5 ml/min. Detection: UV 254 nm.

EXAMPLE 2

Preparation of an adriamycin-phthalic acid-γ-cyclodextrin conjugate (APC)

γ-CD (520 mg, 0.4 mmol) and 118 mg (0.8 mmol) of phthalic anhydride were dissolved in 10 ml of DMF, and 140 μl (1.0 mmol) of triethylamine was then added, followed by conducting the reaction at room temperature for 2 hours. To this solution was added 257 mg (0.4 mmol) of 14-bromodaunomycin hydrochloride, and the reaction, was run at room temperature for 15 hours. Twenty milliliters of chloroform was added to the reaction mixture, and the resulting precipitate was filtered, washed with 20 ml of a chloroform/methanol (1:1) mixture and then dried to obtain 677 mg of a red powder. Further, mg of the powder was purified by ODS column (ODS-A 120-350/250 of YMC CO., LTD.; eluent - water/-acetonitrile/acetic acid=700:300:1; column diameter 1.6 cm, height 20 cm), and fractions having purity of 99% or higher were collected under conditions of HPLC-1 to be described later to provide 38 mg of the above-captioned compound (APC). APC is composed of three main components (Products 1–3).

Physicochemical properties of this compound are shown below.

UV visible (in water; λmax): 483, 286, 250, 234 nm.

Adriamycin content of the product by 484 nm absorbance: 25.8 %.

IR (KBr): 3330, 2900, 1720, 1605, 1580, 1400, 1280, 1150, 1020 cm$^{-1}$.

HPLC-1: APC-(products 1-3) retention time=2.5 minutes. Column: YMC-Pack A-312 S-5 120A ODS. Mobile phase: 0.05M ammonium formate buffer (pH=4.0):acetonitrile=6.4. Flow rate: 1 ml/min. Detection: UV 254 nm.

HPLC-2: APC-product 1 retention time=3.5 minutes. APC-product 2 retention time=4.0 minutes. APC-product 3 retention time=5.0 minutes. Column: YMC-Pack A-312 S-5 120A ODS Mobile phase: 0.05M ammonium formate buffer. (pH=4.0):methanol=2:3. Flow rate: 1.5 ml/min. Detection: UV 254 nm.

EXAMPLE 3

FAB MS (matrix: glycerin): positive: 1397 ([M+H]+), negative: 1395.

([M-H]), $^1$H-NMR (400 MHz, in DMF-d$_7$. 40° C.) δ(ppm): 2.44-2.63 (4H, m, succinyl-methylene, 4.14 (1H, dd, J=6.6, 11.5 Hz, H-6'''a), 4.55 (1H, d, J=11.5 Hz, H-6'''b).

Next, 220 mg (0.157 mmol) of purified 6-SC was dissolved in 4.4 ml of DMF, and 44 μl (0.315 mmol) of triethylamine was then added. With stirring, 100 mg (0.157 mmol) of 14-bromodaunomycin hydrochloride was added, and the reaction was run at room temperature for 2 hours. Under ice cooling, 13 ml of chloroform was added to obtain a precipitate. The precipitate was filtered, washed with 15 ml of a chloroform/methanol (2:1) mixture and dried to afford 219 mg of a red powder. This powder was purified by ODS column (ODS-A 120-350/250 or YMC CO., LTD.; eluent−0.1% acetic acid solution/acetonitrile=650:200; column diameter 2.3 cm, height 17 cm) to provide mg of the above-captioned compound (6-

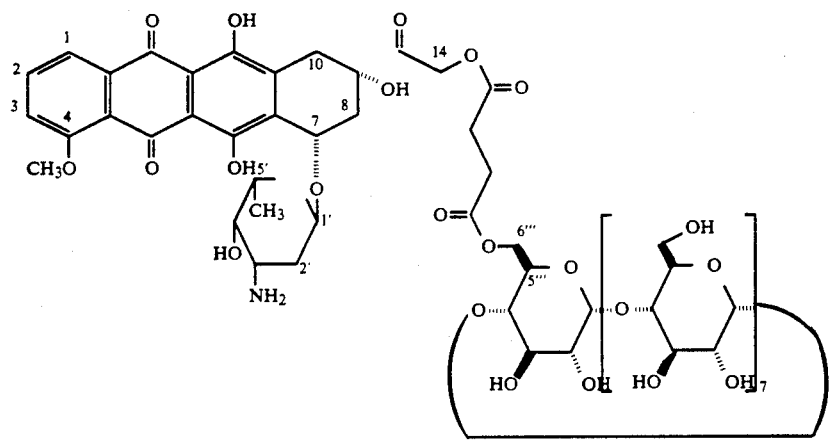

Preparation of an adriamycin (14-position)-succinic acid (6-position) γ-cyclodextrin conjugate (6-ASC)

γ-CD (1,020 mg, 0.786 mmol) was suspended in 1 ml of N,N-dimethylformamide (hereinafter abbreviated as "DMF"), and 5 ml of pyridine was further added and dissolved therein. With stirring, 94.4 mg (0.943 mmol) of succinic anhydride was added, and the reaction was run at room temperature for 18 hours. The reaction mixture was poured in 100 ml of chloroform to obtain a precipitate. The precipitate was filtered, washed with 20 ml of chloroform, and then dried at 60° C. to obtain 1,152 mg of a white powder. The powder was further washed with 20 ml of methanol, and then dried at 60° C. to afford 496 mg of 6-O-succinyl γ-cyclodextrin (hereinafter abbreviated as "6-SC"; containing about 60 mol % as 6-SC).

Crude 6-SC (496 mg) was purified by ODS column (ODS-A 120-350/250 or YMC CO., LTD.: eluent - water/methanol=7:1 to 3:1; column diameter 3 cm, height 25 cm) to provide 220 mg of 6-SC.

Physicochemical properties of this compound are shown below.

ASC).

Physicochemical properties of this compound are shown below.

UV visible (in water; λmax): 482, 289, 254, 234 nm.

IR (KBr): 3387, 2926, 1730, 1622, 1581, 1415, 1157, 1080, 1026 cm$^{-1}$.

FAB MS (matrix: glycerin/thioglycerin=1/1 [V/V]). positive: 1922 ([M+H]+), negative: 1920. ([M-H]), $^1$H-NMR (400 MHz, in DMF-d$_7$: adriamycin portion δ(ppm): 1.28(3H, d, J=6.6Hz, 5'—CH$_3$), 1.86(1H, brd, J=12Hz, H-2'a), 2.02(1H, brt, J=12Hz, H-2'b), 2.23(1H, dd, J=5.1, 14Hz, H-8a), 2.50(1H, d, J=14Hz, H-8b), 3.02(1H, d, J=18Hz, H-10a), 3.21(1H, d, J=18Hz, H-10b), 4.10(3H, s, 4-OCH$_3$), 4.35(1H, q, J=6.6Hz, H-5'), 5.14(1H, brs, H-7), 5.34(1H, d, J=18, H-14a), 5.41(1H, d, J=18, H-14b), 5.43(1H, d, J=3.7Hz, H-1'), 7.73(1H, m, H-3), 7.97(2H, m, H-1, H-2) spacer portion (succinic acid) δ(ppm): 2.78 (4H, m, —CH$_2$—). γ-CD bound portion δ(ppm): 3.98(1H, m, H-5'''), 4.30(1H, dd, J=5.1, 11Hz, H-6'''a), 4.44(1H, d, J=11Hz, H-6'''b).

EXAMPLE 4

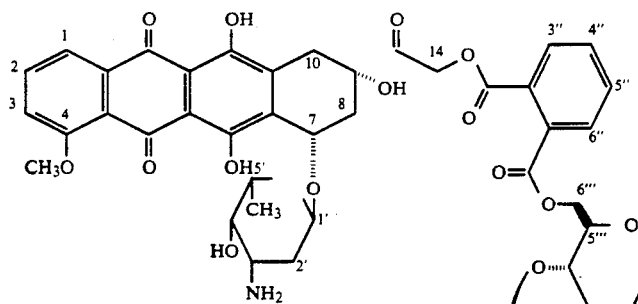
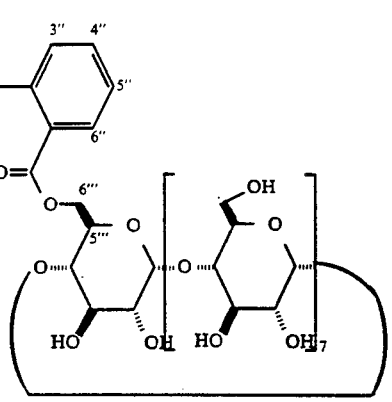

Preparation of an adriamycin (14-position)-phthalic acid-(6-position) γ-cyclodextrin conjugate (6-APC)

γ-CD (1,990 mg, 1.53 mmol) was dissolved in 10 ml of DMF, and 3.3 ml of pyridine was added. With stirring, 75.5 mg (0.510 mmol) of phthalic anhydride was added, and the reaction was run at room temperature for 3 hours. The reaction mixture was poured in 100 ml of chloroform to obtain a precipitate. Said precipitate was filtered, washed with 50 ml of chloroform and then dried at 60° C. to obtain 2,170 mg of a white powder. This powder was further washed with 40 ml of methanol, and then dried at 60° C. to obtain 1,980 mg of 6-O-phthaloyl γ-cyclodextrin (hereinafter abbreviated as "6-PC": containing about 35 mol % as 6-PC).

Part of the above compound was purified as in Example 3 to obtain purified 6-PC.

Physicochemical properties of this compound are shown below.

FAB MS: (matrix: glycerin) positive: 1455 ($[M+H]^+$). (matrix: glycerin/thioglycerin=1/1 [V/V]). negative: 1443 ($[M-H]^-$). $^1$H-NMR (400 MHz, in DMSO-$d_6$ 60°) δ(ppm): 3.90(1H, m, H-5'''), 4.23(1H, dd, J=6.2, 11Hz, H-6'''a), 4.58(1H, d, J=11Hz, H-6'''b), 7.40-7.62 (4H, m, phthaloyl-H).

Crude 6-Pc (containing 35 mol % as 6-PC; 1,200 mg, about 0.3 mmol) was dissolved in 12 ml of DMF, and 84 μl (0.603 mmol) of triethylamine was added. With stirring, 188 mg (0.29 mmol) of 14-bromodaunomycin hydrochloride was added, and the reaction was run at room temperature for 2 hours. Under ice cooling, 36 ml of chloroform was added to obtain a precipitate. The precipitate was filtered, washed with 30 ml of a chloroform/methanol mixture (2:1), and dried to obtain 1,393 mg of a red powder. The powder was purified by ODS column (ODS-A 120-350/250 of YMC CO., LTD.: eluent - 0.1% acetic acid solution/acetonitrile=650:200, column diameter 3 cm, height 24 cm) to obtain 237 mg of the above-captioned compound (6-APC).

Physicochemical properties of this compound are shown as follows.

UV visible (in water; λmax): 482, 285, 252, 233 nm.

IR (KBr): 3400, 2935, 1726, 1620, 1581, 1414, 1286, 1155, 1080, 1028 cm$^{-1}$.

FAB MS (matrix: glycerin/thioglycerin=1/1 [V/V]): positive: 1970 ($[M+H]^+$), negative: 1968 ($[M-H]^-$), $^1$H-NMR (400 MHz, in DMSO-$d_6$): adriamycin portion δ(ppm): 1.19(3H, d, J=6.6Hz, 5'—CH$_3$), 1.67(1H, brd, J=12Hz, H-2'a), 1.86(1H, m, H-2'b), 2.17(1H, m, H-8a), 2.32(1H, d, J=13Hz, H-8b), 2.94(1H, d, J=18Hz H-10a), 3.11(1H, d, J=18Hz, H-10b), 3.99(3H, s, 4—OCH$_3$), 4.22(1H, q, J=6.6Hz, H-5'), 5.00(1H, brs, H-7), 5.32(1H, brs, H-1'), 5.45(2H, brs, H-14), 7.66(1H, m, H-3), 7.92(2H, m, H-1, H-2). spacer portion (phthalic acid) δ(ppm): 7.72(2H, m, H-4", H-5"), 7.80, 7.86(1Hx2, mx2, H-3", H-6"). γ-CD bound portion δ(ppm): 3.95(1H, m, H-5'''), 4.36(1H, m, H-6'''a), 4.53(1H, d, J-11Hz, H-6'''b).

EXAMPLE 5

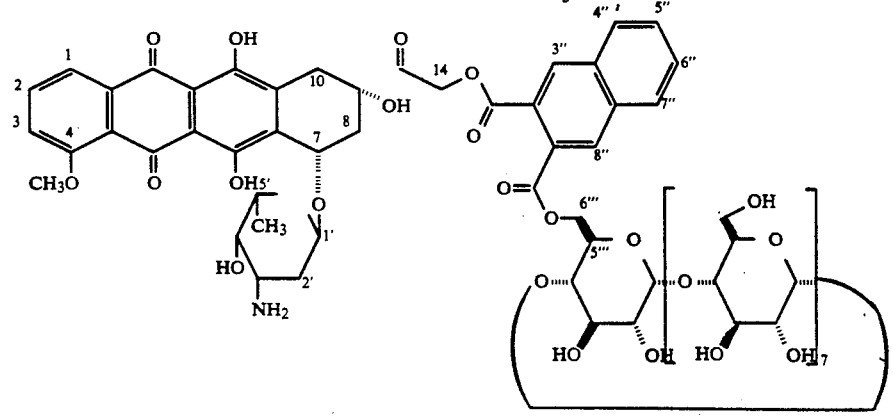

Preparation of an adriamycin
(14-position)-naphthalenedicarboxylic acid-(6-position)
γ-cyclodextrin conjugate (6-ANC)

γ-CD (1,016 mg, 0.783 mmol) was suspended in 1 ml 8.49(1Hx2, sx2, H-3", H-8"). γ-CD bound portion
δ(ppm): 4.01(1H, m, H-5'''), 4.39(1H, m, H-6'''a),
4.59(1H, brd, J=11Hz, H-6'''b).

EXAMPLE 6

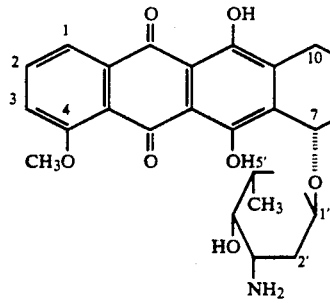
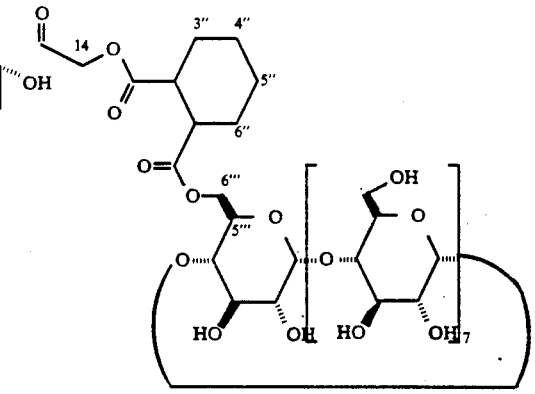

of DMF, and 5 ml of pyridine was added and dissolved. With stirring, 124 mg (0.626 mmol) of 2,3-naphthalenedicarboxylic anhydride was added, and the reaction was run at room temperature for 20 hours. The reaction mixture was poured in 100 ml of chloroform to obtain a precipitate. The precipitate was filtered, washed with 20 ml of chloroform, and then dried at 60° C. to obtain 1,160 mg of a grayish white powder. This powder was further washed with 20 ml of methanol, and then dried at 60° C. to obtain 1,034 mg of 6-O-(2,3-naphthalenedicarboxylic acid) γ-cyclodextrin monoester (hereinafter abbreviated as "6-NC"; containing about 70 mol % as 6-NC).

Six hundred milligrams (about 0.29 mmol) of crude 6-NC (containing about 70 mol % as 6-NC) were dissolved in 10 ml of DMF, and 81 μl (0.58 mmol) of triethylamine was added. With stirring, 187 mg (0.29 mmol) of 14-bromodaunomycin hydrochloride was added was added thereto, and the reaction was run at room temperature for 1.5 hours. Under ice cooling, 25 ml of a chloroform/methanol (4:1) mixture was poured to obtain a precipitate. The precipitate was washed with 20 ml of a chloroform/methanol (2:1) mixture and then dried to afford 789 mg of a red powder. The powder was purified by ODS column (ODS-A 120-350/250 or YMC CO., LTD.; eluent−0.1% acetic acid solution-/acetonitrile=600:200; column diameter 3 cm, height 21 cm) to afford 205 mg of the above-captioned compound (6-ANC).

Physicochemical properties of this compound are shown below.

UV visible (in water; λmax): 486, 338, 285(s), 236 nm.
IR (KBr): 3377, 2934, 1724, 1620, 1583, 1414, 1213, 1155, 1080, 1025 cm$^{-1}$.

FAB MS (matrix: glycerin/thioglycerin=1/1 [V/V]): positive: 2020 ([M+H]$^+$.

$^1$H-NMR (400 MHz, in DMSO-d$_6$): adriamycin portion δ(ppm): 1.21(3H, d, J=6.6Hz, 5'CH$_3$), 1.69(1H, brd, J=12Hz, H-2'a), 1.90(1H, m, H-2'b), 2.20(1H, m, H-8a), 2.34(1H, d, J=13Hz, H-8b), 2.98(1H, d, J=18Hz, H-10a), 3.13(1H, d, J=18Hz, H-10b), 4.00(3H, s, 4-OCH$_3$), 4.23(1H, q, J=6.6Hz, H-5'), 5.02(1H, brs, H-7), 5.33(1H, brs, H-1'), 5.49(2H, brs, H-14), 7.69(1H, m, H-3), 7.92(2H, m, H-1, H-2). spacer portion (naphthalenedicarboxylic acid) (ppm) 7.75(2H, m, H-5", H-6"), 8.18(2H, dd, J=3.3, 5.9Hz, H-4" H-7") 8.43, Preparation of an adriamycin
(14-position)-ciscyclohexanedicarboxylic
acid-(6-position) γ-cyclodextrin conjugate (6-ACC)

γ-CD (1,017 mg, 0.784 mmol) was suspended in 1 ml of DMF, and 5 ml of pyridine was further added and dissolved. With stirring, 123 mg (0.796 mmol) of ciscyclohexanedicarboxylic anhydride was added, and the reaction was run at room temperature for 20 hours. The reaction mixture was poured in 100 ml of chloroform to obtain a precipitate. The precipitate was filtered, washed with 20 ml of chloroform and then dried at 60° C. to afford 1,198 mg of 6-O-(cis-cyclohexanedicarboxylic acid)-cyclodextrin monoester hereinafter abbreviated as "6-CC": containing about 50 mol % as 6-CC).

Crude 6-CC (1,198 mg; containing about 50 mol % as 6-CC) was purified by ODS column (ODS-A 120-350/250 of YMC CO., LTD.; eluent - water/methanol=5:1 to 1:1; column diameter 3 cm, height 25 cm) to obtain 419 mg of 6-CC.

Physicochemical properties of this compound are shown below.

FAB MS (matrix: glycerin): positive: 1451 ([M+H]$^+$), negative: 1499 ([M−H]$^-$). $^1$H-NMR (400 MHz, in DMSO-d$_6$, 60° C.) δ(ppm): 1.36(4H, m, H-4", H-5"), 1.67, 1.90(2Hx2, mx2, H-3", H-6"), 2.72(2H, m, H-2", H-7"), 3.77(1H, dd, J=5.1, 10.3Hz, H-5'''), 4.00(1H, dd, J=5.1, 11.5Hz, H-6'''a) 4.43C1H, d, J=11.5Hz, H-6'''b).

Purified 6-CC (105 mg, 0.0724 mmol) was dissolved in 4 ml of DMF, and 20 μl (0.145 mmol) was added. With stirring, 46.6 mg (0.0724 mmol) of 14-bromodaunomycin hydrochloride was added, and the reaction was run at room temperature for 1.5 hours. Under ice cooling, 20 ml of chloroform and 10 ml of isoppropyl ether were added to obtain a precipitate. The precipitate was washed with a mixed solvent of 5 ml of chloroform and 5 ml of isopropyl ether to afford 152 mg of a crude 6-ACC powder. The powder was purified by ODS column (ODS-A 120-350/250 of YMC CO., LTD.; eluent−0.1 acetic acid solution/acetonitrile=600:200; column diameter 1.6 cm, height 21 cm) to provide 87.5 mg of the above-captioned compound (6-ACC).

Physicochemical properties of this compound are shown below.

UV visible (in water; λmax): 481, 291, 254, 234 nm.
IR (KBr): 3403, 2936, 1730, 1620, 1583, 1415, 1284, 1211, 1157, 1080 cm$^{-1}$.

FAB MS (matrix: glycerin/thioglycerin=1/1 [V/V]: positive: 1976 ([M+H]$^+$), negative: 1974 ([M−H]$^-$). $^1$H-NMR (400 MHz, in DMSO-d$_6$: adriamycin portion δ(ppm): 1.16(3H, d, J=6.6Hz, 5'-CH$_3$), 1.66(1H, brd, J=11Hz, H-2'a), 1.86(1H, m, H-2'b), 2.12(1H, m, H-8a), 2.24(1H, brd, J=14Hz, H-8b), 2.87(1H, d, J=18.5Hz, H-10a), 3.06(1H, d, J=18.5Hz, H-10b), 3.99(3H, s, 4-OCH$_3$), 4.18(1H, a, J=6.6Hz, H-5'), 4.97(1H, brs, H-7), 5.10(1H, d, J=17Hz, H-14a), 5.29(1H, d, J=17Hz, H-14b), 5.30(1H, brs, H-1'), 7.66(1H, m, H-3), 7.92(2H, m, H-1, H-2). spacer portion (cis-cyclohexanedicarboxylic acid) δ(ppm): 1.30–1.50(4H, m, H-4", H-5"), 1.69–1.82(2H, m, H-3"a, H-6"a), 1.86(1H, m, H-6"b), 1.98(1H, m, H-3"b), 2.85(1H, m, H-7"), 3.02(1H, m, H-2") γ-CD bound portion (ppm): 3.78(1H, m, H-5'''), 4.03(1H, m, H-6'''a), 4.41-(1H, brd, J=11Hz, H-6'''b).

EXAMPLE 7

Preparation of a [adriamycin (14-position)-(phthalic acid)]2-(6-position) γ-cyclodextrin conjugate (A2P2C)

γ-CD (1,297 mg, 1 mmol) was suspended in 1.3 ml of DMF, and 6.5 ml of pyridine was added and dissolved. With stirring, 296 mg (2 mmols) of phthalic anhydride was added, and the reaction was run at room temperature for 5 hours. The reaction mixture was poured in 60 ml of chloroform to obtain a precipitate. The precipitate was filtered, washed with 50 ml of chloroform and then dried to obtain 1,400 mg of 6,6'-di-O-phthaloyl γ-chyclodextrin (hereinafter abbreviated as "6,6'-P2C"). The crude powder (1,350 mg) was purified by ODS column (ODS-A 120-350/250 of YMC C., LTD.; eluent - water/methanol=5:1; column diameter 3 cm, height 27 cm) to afford 570 mg of 6,6'-P2C.

Physicochemical properties of this compound are shown below.

FAB MS (matrix: glycerin). positive: 1593([M+H]$^+$) negative: 1591([M−H]$^-$). $^1$H-NMR (400 MHz, in DMSO-d$_6$, 50° C.) δ(ppm): 3.9(2H, m, H-5'''), 4.25(2H, m, H-6'''a), 4.55(2H, m, H-6'''b), 7.4–7.6(8H, m, phthaloyl-H).

Purified 6,6'-P2C (413 mg, about 0.26 mmol) was dissolved in 8 ml of DMF, and 145 μl (1.04 mmols) of triethylamine was added. With stirring, 418 mg (0.65 mmol) of 14-bromodaunomycin hydrochloride was added, and the reaction was run at room temperature for 2 hours. Under ice cooling, 24 ml of chloroform was poured to obtain a precipitate. The precipitate was filtered, washed with 20 ml of ethanol and then dried to obtain 723 mg of a red powder. The powder was purified by ODS column (ODS-A 120-350/250 or YMC CO., LTD.; eluent−0.1% acetic acid solution/acetonitrile=2:1; column diameter 3 cm, height 25 cm, 15 g/fraction). Crude A2P2C-I (35 mg) was obtained from the fractions 12 and 13, and A2P2C-II (20 mg) from the fractions 18 and 19. Crude A2P2C-I was purified again by ODS column (ODS-A 120–350/250 of YMC CO., LTD.; eluent - 0.1% acetic acid solution/methanol=2:3; column diameter 2.2 cm, height 20 cm) to provide 12 mg of A2P2C-I.

Physicochemical properties of these compounds are shown below.

A2P2C-I

HPLC-1: A2P2C-I retention time=6.5 minutes Column: YMC-Pack A-312 S-5 120A ODS Mobile phase: 0.05M ammonium formate buffer. (pH=4.0):methanol=2:3. Flow rate 1.5 ml/min. Detection: UV 254 nm.

UV visible (in water; λmax): 485, 234 nm.
IR (KBr): 3389, 2937, 1724, 1618, 1581, 1410, 1286, 1155, 1080, 1028 cm$^{-1}$.

$^1$H-NMR (400 MHz, in DMSO-d$_6$) δ(ppm): 1.2(6H, d, 5'-CH$_3$x2), 3.8–4.1(8H, m, γCD bound portion H-5x2, 4-OCH$_3$x2), 4.8–5.0(10H, m, CD-H-1, H-7x2), 5.3–5.6(6H, m, H-1'x2, H-14x4), 7.3–8.0(14H, m, H-1x2, H-2x2, H-3x2, phthaloyl Hx2).

A2P2C-II

HPLC-1: A2P2C-II retention time=9.2 minutes. Column YMC-Pack A-312 S-5 120A ODS. Mobile phase: 0.05M ammonium formate buffer. (pH=4.0): methanol=2:3. Flow rate: 1.5 ml/min. Detection: UV 254 nm.

UV visible (in water; λmax): 488, 233 nm.
IR (KBr): 3387, 2936, 1724, 1618, 1581, 1412, 1286, 1155, 1080, 1028 cm$^{-1}$.

$^1$H-NMR (400 MHz, in DMSO-d$_6$) δ(ppm): 1.2(6H, brs, 5'-CH$_3$x2), 4.8–5.0(10H, m, CD-H-1, H-7x2), 7.3–8.0(14H, m, H-1x2, H-2x2, H-3x2, phthaloyl-Hx2).

From the foregoing physicochemical properties, it is found that A2P2C-I and A2P2C-II have respectively such a structure that two (adriamycin-phthalic acid) units are bound to one CD, and that A2P2C-I is different from A2P2C-II in binding sites of the units to CD.

EXAMPLE 8

Preparation for injection of an adriamycindicarboxylic acid-γ-cyclodextrin conjugate Fifty milligrams of the adriamycin derivative of this invention and 100 mg of D-mannitol were taken and dissolved in distilled water. The solution was sterilized by a membrane filter, and further lyophilized to form a preparation for injection.

What is claimed is:

1. A compound of formula (I)

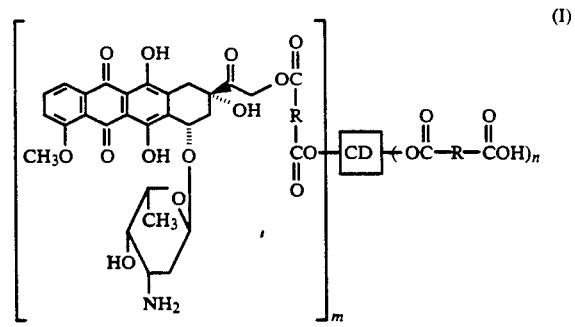

wherein
R is a divalent hydrocarbon group selected from the group consisting of C$_1$-C$_6$ alkylene, —C≡C—, C$_5$-C$_7$ cycloalkylene, 1,2-phenylene and 2,3- and 1,8-naphthalene,
CD is a cyclodextrin residue,
m is 1 to 8, and
n is 0 to 8.

2. The compound of claim 1 wherein R is ethylene, 1,2- or 1,3-propylene, 1,2-, 1,3- or 1,4-butylene, 1,2-cyclohexylene, 1,2-phenylene, or 2,3- or 1,8-naphthalene.

3. The compound of claim 1 wherein CD is a γ-cyclodextrin residue.

4. The compound of claim 1 wherein m is 1 or 2, and n is 0 to 2.

5. The compound of claim 1 wherein R is ethylene, CD is a γ-cyclodextrin residue, m is 1, and n is 0.

6. The compound of claim 1 wherein R is 1,2-phenylene, CD is a γ-cyclodextrin residue, m is 1 or 2, and n is 0.

7. The compound of claim 1 wherein R is 2,3- or 1,8-naphthalene, CD is a γ-cyclodextrin residue, n is 1, and n is 0.

8. The compound of claim 1 wherein R is 1,2-cyclohexylene, CD is a γ-cyclodextrin residue, m is 1, and n is 0.

* * * * *